(12) United States Patent
Richmond

(10) Patent No.: US 10,786,425 B2
(45) Date of Patent: Sep. 29, 2020

(54) METHOD OF PROVIDING MOBILE THERAPY

(71) Applicant: Lolita Richmond, Willoughby, OH (US)

(72) Inventor: Lolita Richmond, Willoughby, OH (US)

(*) Notice: Subject to any disclaimer, the term of this patent is extended or adjusted under 35 U.S.C. 154(b) by 1028 days.

(21) Appl. No.: 14/688,175

(22) Filed: Apr. 16, 2015

(65) Prior Publication Data

US 2015/0209223 A1 Jul. 30, 2015

Related U.S. Application Data

(63) Continuation-in-part of application No. 13/713,656, filed on Dec. 13, 2012, now abandoned.

(51) Int. Cl.
*A61H 33/00* (2006.01)
*G06F 19/00* (2018.01)
(Continued)

(52) U.S. Cl.
CPC ........... *A61H 33/0087* (2013.01); *A61H 9/00* (2013.01); *A61H 9/0007* (2013.01);
(Continued)

(58) Field of Classification Search
CPC ...... A61H 3/00; A61H 2003/001; A61H 9/00; A61H 9/0007; A61H 9/0021; A61H 2009/0014; A61H 2009/0035; A61H 2009/0042; A61H 33/00; A61H 33/0087; A61H 33/0091; A61H 33/02; A61H 33/06; A61H 33/066; A61H 33/10; A61H 33/14; A61H 33/60; A61H 33/6005; A61H 2033/068; A61H 2035/004; A61H 99/00; A61H 2201/01; A61H 99/0157; A61H 2203/02; G16H 40/20; A61G 7/10;
(Continued)

(56) References Cited

U.S. PATENT DOCUMENTS 5,253,410 A * 10/1993 Mortenson .............. B60P 1/431
 14/71.1
5,401,078 A * 3/1995 Riach ...................... A47C 7/503
 297/19

(Continued)

FOREIGN PATENT DOCUMENTS

JP 2007101156 A * 4/2007

*Primary Examiner* — Colin W Stuart
(74) *Attorney, Agent, or Firm* — Fay Sharpe LLP

(57) ABSTRACT

A method for a mobile therapy provider to provide mobile therapy to a patient is disclosed. The mobile therapy provider receives an authorized prescription to provide therapy services, such as water therapy services, to the patient. The mobile therapy provider also verifies that medical insurance is available to the patient to cover the cost of the therapy. An appointment is scheduled with the patient to provide the mobile therapy services at an agreed upon location. A mobile therapy vehicle having therapy equipment is dispatched to the location agreed upon with the patient. An attending therapist provides the patient with the required type and scope of therapy in the mobile therapy vehicle. The results of therapy session are sent by the mobile provider to the insurance provider for payment and to the licensed health care professional.

9 Claims, 4 Drawing Sheets

(51) Int. Cl.
　　*G16H 40/20* (2018.01)
　　*A61H 9/00* (2006.01)
　　*A61G 7/10* (2006.01)
　　*A61G 3/06* (2006.01)
　　*A61H 35/00* (2006.01)
　　*A61H 99/00* (2006.01)

(52) U.S. Cl.
　　CPC ........... *A61H 9/0021* (2013.01); *A61H 33/00* (2013.01); *A61H 33/60* (2013.01); *A61H 33/6005* (2013.01); *G06F 19/328* (2013.01); *G06F 19/3481* (2013.01); *G16H 40/20* (2018.01); *A61G 3/061* (2013.01); *A61G 7/1005* (2013.01); *A61H 99/00* (2013.01); *A61H 2009/0035* (2013.01); *A61H 2009/0042* (2013.01); *A61H 2035/004* (2013.01); *A61H 2201/0157* (2013.01); *A61H 2201/0207* (2013.01); *A61H 2203/02* (2013.01)

(58) Field of Classification Search
　　CPC .. A61G 7/1001; A61G 7/1003; A61G 7/1005; A61G 13/009
　　USPC ......... 601/154, 160, 167; 180/313; 119/703; 705/2, 3
　　See application file for complete search history.

(56) References Cited

U.S. PATENT DOCUMENTS

| | | | | |
|---|---|---|---|---|
| 5,422,014 | A * | 6/1995 | Allen | C02F 1/008 210/139 |
| 6,070,278 | A * | 6/2000 | Smith | A61G 7/1005 4/496 |
| 6,082,799 | A * | 7/2000 | Marek | B60P 3/14 296/19 |
| 6,250,336 | B1 * | 6/2001 | Murphey | B60R 15/00 137/539 |
| 8,453,275 | B2 * | 6/2013 | May | A61H 33/005 4/507 |
| 10,034,813 | B1 * | 7/2018 | Silver | A61B 19/2203 |
| 2011/0185979 | A1 | 8/2011 | Dunagan | |
| 2011/0294625 | A1 * | 12/2011 | Flake | A63B 22/0264 482/54 |
| 2012/0259651 | A1 * | 10/2012 | Mallon | G06Q 10/06 705/2 |
| 2015/0379199 | A1 * | 12/2015 | Tambasco, Jr. | H04N 5/44 705/3 |

* cited by examiner

METHOD OF PROVIDING MOBILE THERAPY

CROSS-REFERENCE TO RELATED APPLICATIONS

The present application is a Continuation-In-Part application of U.S. application Ser. No. 13/713,656 filed on Dec. 13, 2012.

TECHNICAL FIELD OF THE INVENTION

The present invention relates to a method of providing mobile therapy and more particularly to providing mobile water therapy with a mobile therapy vehicle.

BACKGROUND OF THE INVENTION

Aquatic therapy is a specialized form of physical or occupational therapy. For years, therapists have realized positive results when applying this water modality to a variety of patient populations. Water has been, and still remains, the best environment to achieve full function regardless of the injury. Water improves motion and flexibility. The warmth of the water, typically about 94° F., and its massaging effects allow muscles to relax while helping to reduce pain. The natural buoyancy reduces gravitational pull and lessens compressive forces, hence making exercises much easier to perform than on land. Best of all, aquatic therapy can be used even if a patient does not know how to swim. The benefits of aquatic therapy are achieved because: warm water facilitates muscle relaxation and increases peripheral circulation; the viscosity of water provides resistance for strength training; warm water stimulates body awareness, balance, and trunk stability; the reduction of gravitational forces in the pool allows the patient to stand and begin gait training and strengthening exercises without causing further damage to healing structures; and the warm water and buoyancy results in decreased pain sensitivity.

Currently patients requiring or prescribed water therapy must seek such treatment at a health facility, such as a local YMCA, a health spa or fitness facility. These establishments require memberships, which are often cost prohibitive for patients within specific demographics such as senior citizens and low income. Moreover, for some patients the treatment may only be needed for a limited amount of time and the investment of an extended membership is unnecessary.

SUMMARY OF THE INVENTION

According to an embodiment of the present invention, there is disclosed a method for a mobile therapy provider to provide mobile therapy to a patient. The method includes the mobile therapy provider receiving an authorized prescription to provide therapy services to the patient. The mobile therapy provider verifies that the authorized prescription was prescribed and supervised by a licensed health care professional by the mobile therapy provider. The mobile therapy provider also verifies that medical insurance is available to the patient from an insurance provider to cover the cost of the therapy. The mobile therapy provider schedules an appointment with the patient by to provide the mobile therapy services at an agreed upon location. Next, the mobile therapy provider dispatches a mobile therapy vehicle having therapy equipment therein to the location agreed upon with the patient at an appointed time. An attending therapist receives instructions from the mobile therapy provider as to the type and scope of therapy required by the patient. The patient is provided with the required type and scope of therapy by the attending therapist in the mobile therapy vehicle. The results of therapy session are recorded and provided to the mobile provider. The results of therapy session are sent by the mobile provider to the insurance provider for payment and to the licensed health care professional.

According to another embodiment of the present invention, there is disclosed a mobile water/aquatic therapy vehicle to provide physical therapy to a patient at a residential home, a nursing home or other type of residential or non-residential living facility. The mobile vehicle includes a box section being equipped with a handicap accessible therapy pool for physical therapy. An hydraulic chair lift system disposed adjacent to the tub to lift the patient when ambulatory into and out of the therapy pool. A door closes a rear opening of the box section and a retractable walk ramp is mounted to the rear of the box section so that the patient can easily enter and exit the interior of the box section.

BRIEF DESCRIPTION OF THE DRAWINGS

The structure, operation, and advantages of the present invention will become further apparent upon consideration of the following description taken in conjunction with the accompanying figures (FIGS.). The figures are intended to be illustrative, not limiting. Certain elements in some of the figures may be omitted, or illustrated not-to-scale, for illustrative clarity. The cross-sectional views may be in the form of "slices", or "near-sighted" cross-sectional views, omitting certain background lines which would otherwise be visible in a "true" cross-sectional view, for illustrative clarity.

In the drawings accompanying the description that follows, both reference numerals and legends (labels, text descriptions) may be used to identify elements. If legends are provided, they are intended merely as an aid to the reader, and should not in any way be interpreted as limiting.

DETAILED DESCRIPTION OF THE PREFERRED EMBODIMENTS

Figure 1:
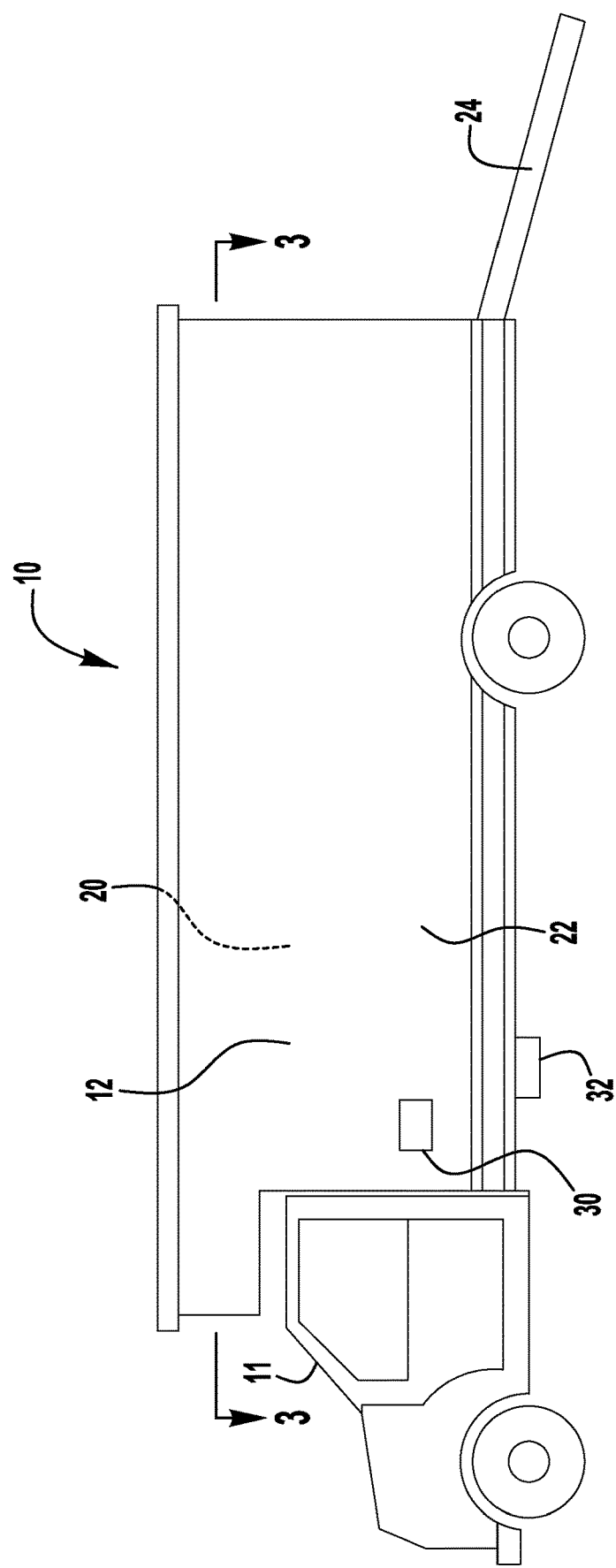
FIG. 1 is a side view of a box or straight truck, in accordance with the present invention.

In the description that follows, numerous details are set forth in order to provide a thorough understanding of the present invention. It will be appreciated by those skilled in the art that variations of these specific details are possible while still achieving the results of the present invention. Well-known processing steps are generally not described in detail in order to avoid unnecessarily obfuscating the description of the present invention.

In the description that follows, exemplary dimensions may be presented for an illustrative embodiment of the invention. The dimensions should not be interpreted as limiting. They are included to provide a sense of proportion. Generally speaking, it is the relationship between various elements, where they are located, their contrasting compositions, and sometimes their relative sizes that is of significance.

In the drawings accompanying the description that follows, often both reference numerals and legends (labels, text descriptions) will be used to identify elements. If legends are provided, they are intended merely as an aid to the reader, and should not in any way be interpreted as limiting.

Water therapy is commonly recommended by physicians for a variety of medical reasons ranging from common and chronic arthritis to rehabilitation following surgery and injuries to complex and terminal muscle problems. Depending upon a patient's physical limitations, getting to a traditional facility could be challenging. Many traditional facilities have limited lifeguard hours and limitations on the staff and hydraulic or other means of getting patients in a pool or therapy pool for water therapy.

The present invention, as shown in FIG. 1, provides a mobile water/aquatic therapy vehicle 10, which includes a cab section 11 and a box section 12. The box section 12 can be approximately 28 feet by 8 feet and is equipped with a handicap accessible hot tub or a therapy pool 13 which provide low-impact cardiovascular exercise, muscle strengthening and muscle regeneration with deep-tissue massage. The therapy pool 13 can include: an underwater treadmill, therapy jets, a moveable floor for variable water depth; underwater cameras and hydro massage. An example of a therapy pool is a HydroWorx pool provided by HydroWorx of Middletown, Pa. Besides the therapy pool 13, the box section 12 can also include equipment to provide various types of water and/or non water physical therapy direct to the patient's door at a residential/patient home, a nursing home or any other type of residential or non-residential living facility.

Figure 2:
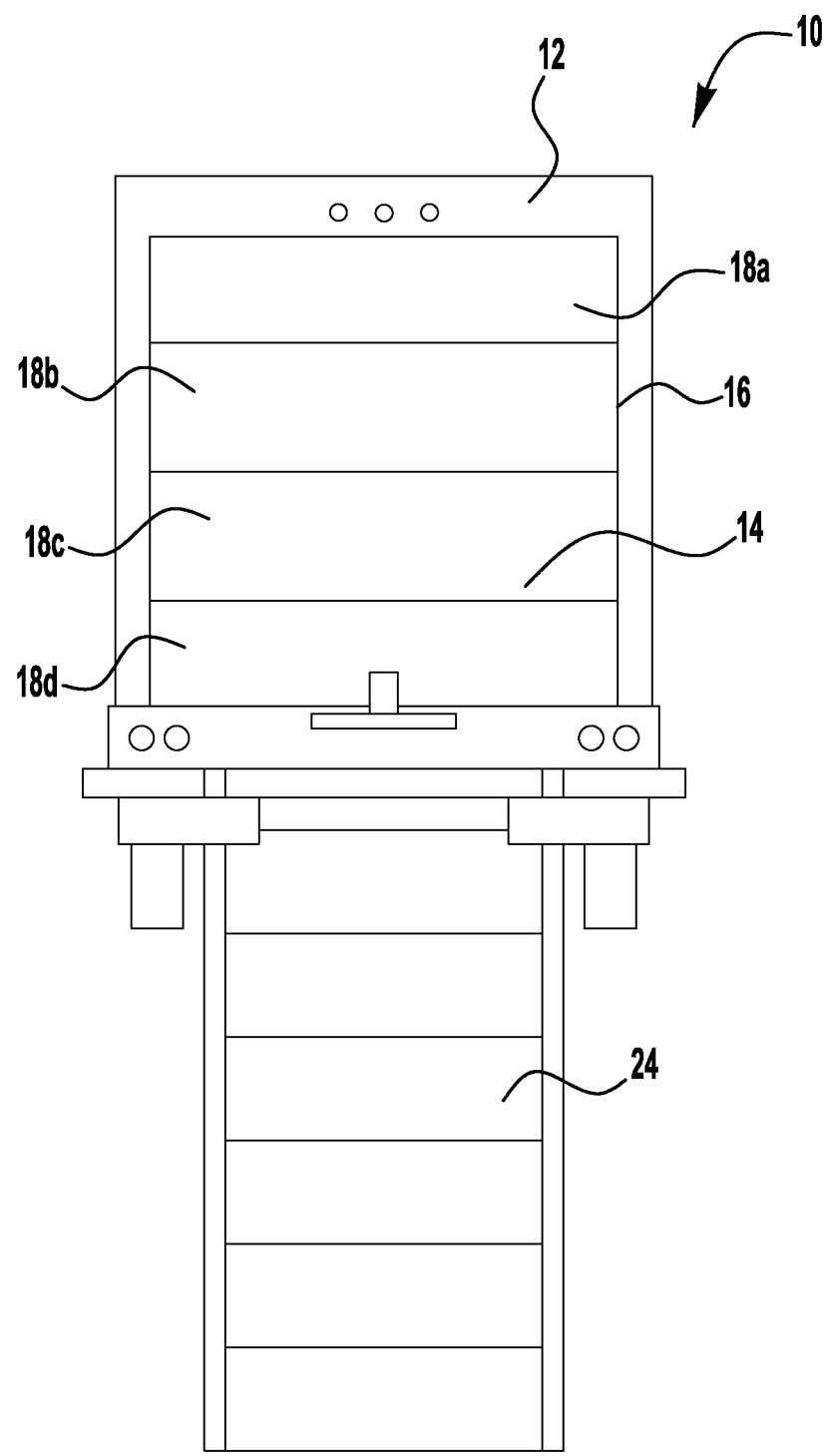
FIG. 2 is a rear view of the truck illustrated in FIG. 1, according to the invention.

Referring to FIG. 2, there is illustrated a rear view of the box section 12 of the truck 10 showing a conventional roll up shutter door 14, typically constructed of either anodized or bright-brushed aluminum for long-lasting durability, closing the rear opening 16 of the box section 12. A low temperature side seal (not shown) between the rear opening 16 of the box section 12 is designed to withstand the cracking and breaking caused by weathering and aging. The shutter door 14 includes a plurality of panels 18a, 18b, 18c, and 18d can be with nylon end-guides to ensure quiet and smooth operation without continual lubrication. Each panel 18a, 18b, 18c, and 18d is inter-sealed with an adjacent panel to prevent the effects of inclement weather, such as freezing rain and sub-zero temperatures from entering into the interior 20 of the box section 12 of the truck 10. Typically, there is a header/counterbalance design that enables the door 14 to "coil up" into a header (not shown).

A retractable, lightweight walk ramp 24 is stored below the box section 12 of truck 10. The ramp can be easily put in place, as shown in FIG. 2, so that a patient or therapist can easily enter and exit by wheel chair or walking the interior 20 of the box section 12. Retractable handrails (not shown) can be provided on the side of the ramp to help a person to safely walk up or down the walk ramp 24.

Figure 3:
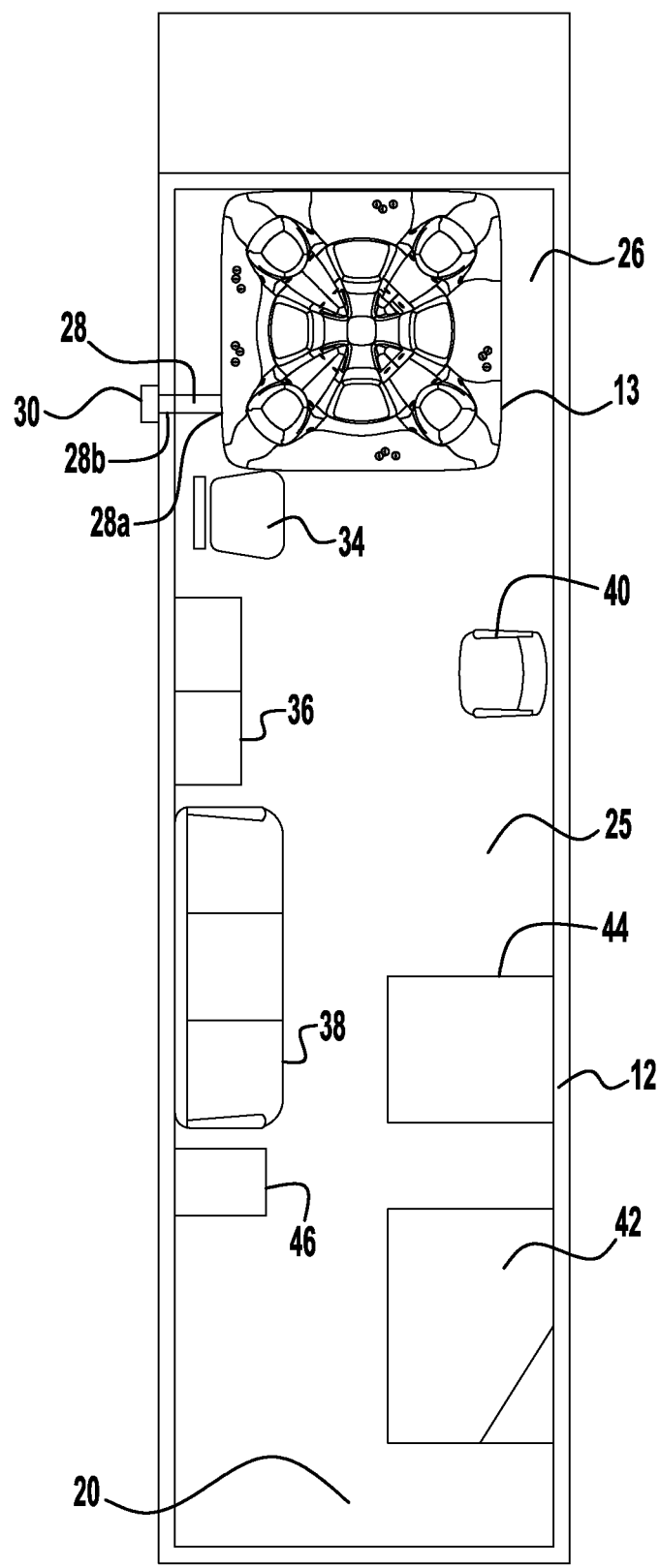
FIG. 3 is a view through the line 3-3 of FIG. 1, according to the invention.

Referring to FIG. 3, there is illustrated the floor plan for the interior 20 of the box section 12. A therapy pool 13 can be mounted to the floor 25 at one end 26 of the box section 12. An inlet water pipe 28 can be connected to the therapy pool 13 at one end 28a and extend to an inlet valve 30 at the opposite end 28b. The inlet valve, as shown in FIG. 1, is mounted through a side wall of the box section 12 so that it can be easily connected to a source of water by any means such as a hose. The inlet water pipe 28 enables the tub 13 to be filled with water. A discharge pipe is mounted to the underside of the tub so that the water in the tub can be easily drained from the tub. A water discharge valve 32 is connecter to the discharge pipe. The water discharge valve 32 will be mounted to the underside of the box section 12 directly below the therapy pool 13 so that the water in the tub can be easily drained from the tub.

A hydraulic chair lift system 34 (with safety straps) is mounted to the floor 25 adjacent to the tub 13. The lift chair 34 is designed to lift ambulatory people into and out of the therapy pool 13. The lift chair 34 includes a seat on which the patient is seated. Then the seat is rotated to a position above the tub. A medical assistant can then lower the seated patient inside the tub to receive the necessary water therapy. The lift chair can then assist the patient to get out of a therapy pool unit.

Other equipment within the box section 12 includes cabinets 36, a sofa 38 and a massage chair 40. The box section 12 can also be fully stocked with clean/fresh/sanitary towels and a receptacle for soiled/used towels and blankets. In addition the vehicle would be equipped with a rear compact disc (CD) to player soothing music to assist the patient in relaxing; aroma-therapy so the patient can relax; a digital video disc (DVD) to play mini movies regarding the benefits of water therapy or other movies. The box unit can be fully stocked with clean, sanitary, warm towels and clean, sanitary warm blankets; a small refrigerator for beverages; and a cabinet for items as needed.

A dressing room 42 can be provided for the patient to change into a bathing suit or dry clothes. A portable rest room 44 with a toilet can be mounted within the box section 12. Also, if desired an enclosed shower 46 can be mounted within the box section 12. The water for the restroom 44 and the shower 46 can be provided by a water tank (not shown). The drains from the restroom 44 and the shower 46 can be collected in a waste tank (not shown) mounted under the box section 12.

Figure 4:
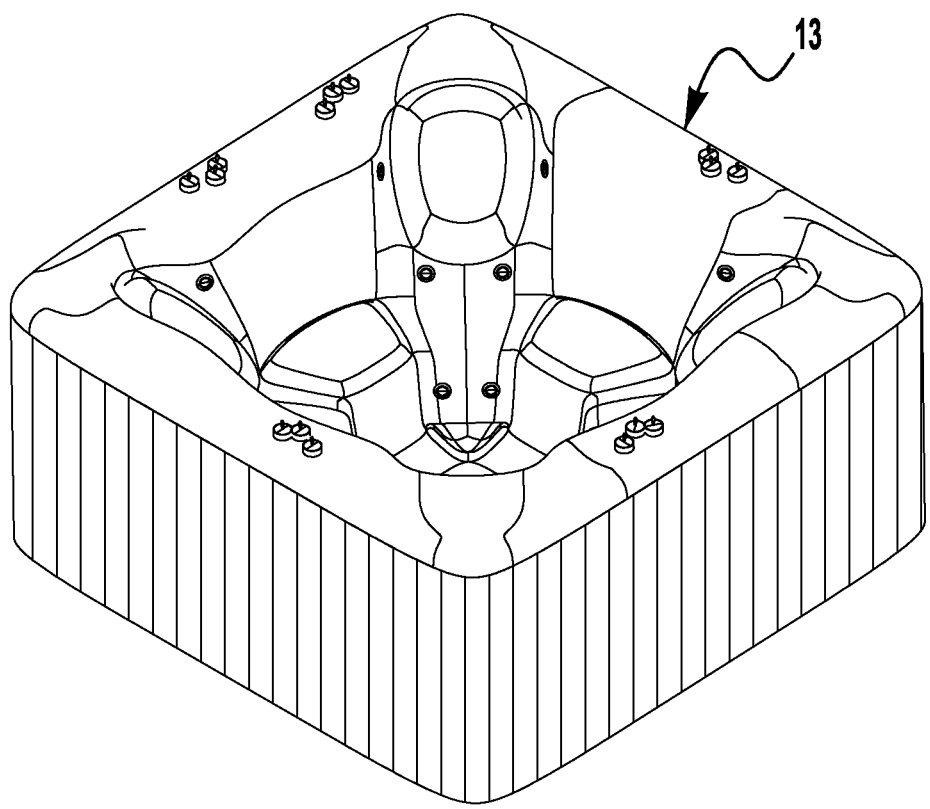
FIG. 4 is a three dimensional view of a therapy pool, according to the invention.

Referring to FIG. 4, there is illustrated a therapy pool 13 that will be a state of the art unit, which will be maintained with clean water and the appropriate chemicals to maintain the sanitation of the unit. The therapy pool 13 will be self contained in the box section 12 of the truck 10 and will not be removed for the purpose of providing therapy. Instead, the water therapeutic treatment will be a mobile water therapeutic treatment. The therapy pool/water therapy tub 13 can be approximately 7 feet in length, 7 feet in width and 3 feet deep and able to accommodate two to four people. The therapy pool 13 can include: automatic filter cycles; freeze protection; digital diagnostics; an un-inhibited polyethylene shell; a quick drain; foam insulation; and a standard/economy program heating system. The therapy pool 13 can be specially fitted with multiple water jets designed to provide water therapy for various extremities.

The power to operate the hot tub and other equipment within the box section 12 of the truck 10 can be provided by a separate electrical generator mounted to the exterior 22 or the interior of the box section. Alternatively, the power can be provided by a generator amounted to the truck engine.

In operation, the mobile water/aquatic therapy vehicle 10, equipped with a therapy pool 13 for various types of water physical therapy will have the ability to drive to the patient's home or nursing home driveway/parking lot to provide mobile water therapy services, typically for up to 20-30 minutes or less depending on physician orders. The number of mobile unit visits and length of time in the mobile therapy pool unit would depend upon physician orders. The mobile water therapy is designed to assist patients with a variety of medical challenges such as arthritis, multiple sclerosis (MS), surgical rehabilitations and more, and any individual who can benefit from water therapy in a small environment.

The therapy pool will be a state of the art unit, which will be maintained with clean water and the appropriate chemicals to maintain the sanitation of the unit. The therapy pool will be self contained in the truck and not removed for the purpose of providing therapy. This is a mobile water therapeutic treatment.

The present invention is also directed to a method of providing mobile water, occupational physical and physical therapy using a vehicle equipped with a handicap accessible therapy pool and other equipment to provide various types of water and/or non water physical therapy direct to the patient's door at a residential/patient home, a nursing home or any other type of residential or non-residential living facility.

Initially, the mobile water, occupational physical and physical therapy provider, also called mobile provider herein, receives an authorized prescription to provide mobile water, occupational physical and/or physical therapy services to a patient. The authorized prescription can be prescribed and supervised by a licensed health care professional such as a physician, a certified physician assistant working under the supervision of a physician or a certified nurse practitioner. The representative of the mobile water, occupational physical and physical therapy provider then verifies that medical insurance is available from an insurance provider to cover the cost of the therapy. If not covered or if a co-pay is required, the patient is contacted and the patient is required to provide a verbal agreement that they will pay the mobile provider any out of pocket costs not covered by their medical insurance.

A representative of the mobile provider then schedules an appointment with the patient to provide the therapy services at an agreed upon location, typically at the patient's residence, a nursing home or any other type of residential or non-residential living facility. The mobile provider then dispatches a mobile water/aquatic therapy vehicle 10 to the location agreed upon with the patient at the appointed time. The mobile provider provides instructions to the attending therapist as to the type and scope of therapy that the patient will require.

Once the mobile water/aquatic therapy vehicle 10 reaches the location of the patient, the attending therapist prepare the therapy equipment in the vehicle for the particular therapy that will be given. For example, the temperature of the therapy pool can be adjusted to the needs of the patient. Next, the back door of the truck is opened and the walk ramp 24 put in place.

The therapist can meet the patient and have them fill out any required forms and pay the out of pocket expenses as needed. Then, the therapist can help the patient to the therapy vehicle and up the walk ramp into the therapy vehicle. The patient can be directed to a dressing room 42 to change into a bathing suit, if the patient requires the use of the therapy pool. Once the patient is dressed, they can be helped into the therapy pool, preferably with the use of a hydraulic chair lift system 34. Once the therapy session in the therapy pool is concluded, the hydraulic chair lift system 34 can lift the patient out of the therapy pool 13. The patient can be directed to the dressing room to change back to dry clothes. The therapist can fill out any forms, such as on a computer, describing the results of the therapy session. The resulting forms can then be uploaded by the mobile provider. The mobile provider can send the results to the insurance company for payment and to the licensed health care professional that prescribed the prescription and is supervising the progress of the patient.

Although the invention has been shown and described with respect to a certain preferred embodiment or embodiments, certain equivalent alterations and modifications will occur to others skilled in the art upon the reading and understanding of this specification and the annexed drawings. In particular regard to the various functions performed by the above described components (assemblies, devices, etc.) the terms (including a reference to a "means") used to describe such components are intended to correspond, unless otherwise indicated, to any component which performs the specified function of the described component (i.e., that is functionally equivalent), even though not structurally equivalent to the disclosed structure which performs the function in the herein illustrated exemplary embodiments of the invention. In addition, while a particular feature of the invention may have been disclosed with respect to only one of several embodiments, such feature may be combined with one or more features of the other embodiments as may be desired and advantageous for any given or particular application.

The invention claimed is:

1. A method for a mobile therapy provider to provide mobile therapy services, comprising:

providing an authorized prescription for a patient to receive mobile therapy services wherein the prescription is authorized by a licensed health care professional, selected from a group consisting of a physician, a certified physician assistant working under the supervision of a physician and a certified nurse practitioner;

receiving the authorized prescription by the mobile therapy provider to provide mobile therapy services to the patient; verifying that the authorized prescription was prescribed and supervised by the licensed health care professional by the mobile therapy provider; verifying that medical insurance is available to cover the mobile therapy services by the mobile therapy provider; scheduling an appointment with the patient by the mobile therapy provider to provide the mobile therapy services at an agreed upon location at a particular time;

dispatching a mobile therapy vehicle including a cab and a box section and having therapy equipment within the box section to the location agreed upon with the patient at an appointed time by the mobile therapy provider;

providing the mobile therapy vehicle with a cab and a box section being equipped with a therapy pool permanently mounted within an interior of the box section to a floor of the box section for physical therapy;

providing the therapy pool including an underwater treadmill, therapy jets, a moveable floor for variable water depth, underwater cameras and hydro massage;

connecting an inlet water pipe at a first end to the therapy pool and connecting the inlet water pipe at a second end to an inlet valve;

mounting the inlet valve to the inlet water pipe through a side wall of the box section so that it can be connected to a source of water;

mounting a water discharge pipe to an underside of the therapy pool so that water in the therapy pool can be drained from the therapy pool;

connecting a water discharge valve to the water discharge pipe, and mounting the water discharge valve to an underside of the box section directly below the therapy pool so that water in the therapy pool can be drained from the therapy pool;

providing the box section with a dressing room, cabinets, a massage chair, and a portable rest room with a toilet;

disposing a hydraulic chair lift system adjacent to the therapy pool and mounting the hydraulic chair lift system to the floor of the box section to lift the patient when ambulatory into and out of the therapy pool;

providing the hydraulic chair lift system with a seat on which the patient is seated and then rotating the seat to a position above the therapy pool and then lowering the seat into the therapy pool whereby the seated patient can receive the necessary water therapy;

providing a roll up shutter door having a plurality of panels inter-sealed with an adjacent panel closing a rear opening of the box section; and storing a retractable walk ramp below the box section and adapting the retractable walk ramp to be mounted to the rear opening into the box section so that the patient can enter and exit the interior of the box section through the rear opening into the box section of the mobile therapy vehicle;

instructing an attending therapist as to the type and scope of mobile therapy services required in accordance with the authorized prescription for the patient by the mobile therapy provider;

providing the required type and scope of mobile therapy services to the patient by the attending therapist representing the mobile therapy provider while the patient is within the mobile therapy vehicle;

recording results of the mobile therapy services and providing the results by the attending therapist to the mobile therapy provider; and sending the results of the mobile therapy services by the mobile therapy provider to an insurance company for payment and to the licensed health care professional.

2. The method of claim 1 wherein the step of scheduling the appointment at an agreed upon location is at the patient's residence, nursing home or non-residential living facility.

3. The method of claim 1 wherein the mobile therapy services provided by the mobile therapy provider are selected from the group consisting of mobile water therapy, occupational therapy and physical therapy.

4. The method of claim 1 wherein the step of providing the mobile therapy services to the patient includes preparing the therapy equipment in the vehicle for the particular therapy required.

5. The method of claim 4 wherein the step of preparing the therapy equipment in the vehicle includes adjusting temperature of the therapy pool to the needs of the patient.

6. The method of claim 5 wherein the step of providing the required mobile therapy services to the patient includes helping the patient into and out of the therapy pool.

7. The method of claim 6 wherein the step of helping the patient into the therapy pool includes lowering the patient into the therapy pool and out of the therapy pool with the hydraulic chair lift system.

8. The method of claim 1 wherein the step of recording results of mobile therapy services and providing the results to the mobile therapy provider includes filling out any forms on a computer describing the results of the mobile therapy services and uploading the results to the mobile therapy provider.

9. A mobile therapy vehicle to provide physical therapy services to a patient at a residential home, a nursing home or non-residential living facility, comprising:

the mobile therapy vehicle including a cab and a box section being equipped with a therapy pool permanently mounted within an interior of the box section to a floor of the box section for physical therapy;

the therapy pool including an underwater treadmill, therapy jets, a moveable floor for variable water depth, underwater cameras and hydro massage;

an inlet water pipe connected at a first end to the therapy pool and connected at a second end to an inlet valve;

the inlet valve mounted to the inlet water pipe through a side wall of the box section so that it can be connected to a source of water;

a water discharge pipe mounted to an underside of the therapy pool so that water in the therapy pool can be drained from the therapy pool;

a water discharge valve connected to the water discharge pipe, the water discharge valve mounted to an underside of the box section directly below the therapy pool so that water in the therapy pool can be drained from the therapy pool;

the box section having a dressing room, cabinets, a massage chair, and a portable restroom with a toilet; a hydraulic chair lift system disposed adjacent to the therapy pool and mounted to the floor of the box section to lift the patient when ambulatory into and out of the therapy pool; the hydraulic chair lift system including a seat on which the patient is adapted to be seated and then the seat is rotated to a position above the therapy pool tub and then lowered into the therapy pool whereby the seated patient can receive necessary water therapy; a roll up shutter door including a plurality of panels inter-sealed with an adjacent panel closing a rear opening of the box section; and a retractable walk ramp stored below the box section and adapted to be mounted to the rear opening into the box section so that the patient can enter and exit the interior of the box section through the rear opening into the box section of the mobile therapy vehicle.

\* \* \* \* \*